United States Patent
Joy et al.

(10) Patent No.: US 11,116,211 B2
(45) Date of Patent: *Sep. 14, 2021

(54) MODIFICATION OF SEGMENTED POLYURETHANE PROPERTIES BY COPOLYMERIZING WITH PENDANT FUNCTIONALIZED DIOLS

(71) Applicants: Abraham Joy, Copley, OH (US); Chao Peng, Tallmadge, OH (US); Zhuoran Li, Akron, OH (US); Nicholas Nun, Akron, OH (US); Apoorva Vishwakarma, Akron, OH (US)

(72) Inventors: Abraham Joy, Copley, OH (US); Chao Peng, Tallmadge, OH (US); Zhuoran Li, Akron, OH (US); Nicholas Nun, Akron, OH (US); Apoorva Vishwakarma, Akron, OH (US)

(73) Assignee: The University of Akron, Akron, OH (US)

( * ) Notice: Subject to any disclaimer, the term of this patent is extended or adjusted under 35 U.S.C. 154(b) by 48 days.

This patent is subject to a terminal disclaimer.

(21) Appl. No.: 16/438,559

(22) Filed: Jun. 12, 2019

(65) Prior Publication Data

US 2019/0297883 A1  Oct. 3, 2019

Related U.S. Application Data

(63) Continuation-in-part of application No. 16/297,933, filed on Mar. 11, 2019, now abandoned.

(60) Provisional application No. 62/640,852, filed on Mar. 9, 2018.

(51) Int. Cl.

| | | |
|---|---|---|
| *C08G 18/38* | (2006.01) | |
| *A01N 33/08* | (2006.01) | |
| *C08G 18/73* | (2006.01) | |
| *C08G 18/75* | (2006.01) | |
| *C08G 18/48* | (2006.01) | |
| *C08G 18/10* | (2006.01) | |
| *C08G 18/24* | (2006.01) | |
| *C08J 5/18* | (2006.01) | |
| *A61L 2/23* | (2006.01) | |
| *C08G 18/32* | (2006.01) | |

(52) U.S. Cl.
CPC .............. *A01N 33/08* (2013.01); *A61L 2/23* (2013.01); *C08G 18/10* (2013.01); *C08G 18/246* (2013.01); *C08G 18/3206* (2013.01); *C08G 18/3821* (2013.01); *C08G 18/4854* (2013.01); *C08G 18/73* (2013.01); *C08G 18/758* (2013.01); *C08J 5/18* (2013.01); *C08J 2375/12* (2013.01)

(58) Field of Classification Search
None
See application file for complete search history.

(56) References Cited

U.S. PATENT DOCUMENTS

| 3,507,830 | A | | 4/1970 | Feinauer |
| 3,699,078 | A | * | 10/1972 | Castro ............... C08G 18/3825 |
| | | | | 528/85 |
| 5,459,222 | A | | 10/1995 | Rodgers et al. |
| 9,593,201 | B2 | | 3/2017 | Joy et al. |
| 9,957,346 | B2 | | 5/2018 | Kennedy et al. |
| 2008/0145338 | A1 | | 6/2008 | Anderson et al. |
| 2010/0178267 | A1 | | 7/2010 | Puerta |
| 2010/0233112 | A1 | | 9/2010 | Hu et al. |
| 2015/0231305 | A1 | | 8/2015 | Gogolewski |
| 2016/0024251 | A1 | | 1/2016 | Joy |
| 2016/0108167 | A1 | * | 4/2016 | Kim ....................... C08G 18/34 |
| | | | | 525/450 |
| 2017/0172147 | A1 | | 6/2017 | Joy et al. |
| 2019/0211135 | A1 | * | 7/2019 | Joy ...................... C08G 18/283 |
| 2019/0276583 | A1 | * | 9/2019 | Joy ...................... C08G 18/4854 |

FOREIGN PATENT DOCUMENTS

| EP | 1905789 | | 4/2008 | |
| JP | 2013087229 A | * | 5/2013 | ............ C08G 18/00 |
| WO | 2010040188 A1 | | 4/2010 | |
| WO | 2011045443 A1 | | 4/2011 | |
| WO | WO-2018039453 A1 | * | 3/2018 | ............ C08G 18/10 |

OTHER PUBLICATIONS

Machine translation of JP-2013087229-A (no date).*
Kang et al.,Polyisobutylene-Based Polyurethanes with Unprecedented Properties and How They Came About, Journal of Polymer Science Part A: Polymer Chemistry 2011, 49, 3891-3904, published online Jul. 11, 2011.
Peng et al., Modification of a conventional polyurethane composition provides significant anti-biofilm activity against *Escherichia coli*, The Royal Society of Chemistry 2018, Polym. Chem., Sep. 2018, 3195-3198, Received Mar. 29, 2018, Accepted May 17, 2018.

(Continued)

*Primary Examiner* — Michael J Feely
(74) *Attorney, Agent, or Firm* — Renner, Kenner, Greive, Bobak, Taylor & Weber

(57) ABSTRACT

A functionalized polyurethane polymer is provided, the polymer defined by the formula

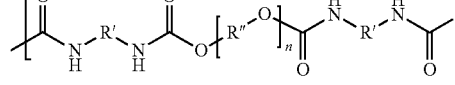

where each R' is independently derived from a diisocyanate, where each R" represents the soft segment of the polymer, where n is the number of repeat units within the soft segment of the polymer, where m is the number of repeating mer units in the polymer, where each E is a pendant-functionalized amide unit chain extender, wherein the nitrogen atom of the amide group is part of the polymer backbone. A method for preparing the polymer is also provided.

19 Claims, 5 Drawing Sheets
(3 of 5 Drawing Sheet(s) Filed in Color)

(56) References Cited

OTHER PUBLICATIONS

Akindoyo et al., Polyurethane types, synthesis and application—a review, The Royal Society of Chemistry 2016, RSC Adv., Jun. 2016, 114453-114482, Received Jun. 4, 2016, Accepted Nov. 21, 2016.
Gokhale et al., A Library of Multifunctional Polysters with "Peptide-Like" Pendant Functional Groups, 2013 American Chemical Society, dx.doi.org/10.1021/bm400697u I Biomacromolecules 2013, 14, 2489-2493.
Mohamed et al., Catalytic polymerization of N,N-diethanol acrylamide with phthalic anhydride in the presence of H-mordenite and Fe-mordenite zeolites, Journal of Molecular Catalysis A: Chemical 211 (2004) 199-208, Received Mar. 20, 2003; accepted Oct. 8, 2003.
Jason Rochette, Photo-Responsive Polyesters for Shape Memory Biomaterials, Polymer Preprints, 2011, 52(1), 121, University of North Carolina—Chapel Hill, North Carolina.
Shukla Bhattacharya, Controlled-Release Polymeric Herbicide Formulations with Pendent 2,4-Dichlorophenoxyacetic Acid, American Chemical Society, 1986, 25, 585-589, Jadavpur University, Calcutta, India.
Lu Chengxun, Synthesis of Flexible Polyesters Containing Nucleic Acid Base Derivatives as Pending Side Chains, Chinese Science Bulletin, 1988, 33, 292, Peking University Beijing.
C.X. Lu, Synthesis of Diols Containing 5-Benzyluracil Base and their Polymers, Journal of Polymer Science: Part A: Polymer Chemistry, 1990, 28, 1329-1340, Peking University, Beijing.
C.X. Lu, Synthesis of Diols Containing Nucleic Acid Bases and Their Polyesters, Journal of Polymer Science: Part A; Polymer Chemistry, 1989, 27, 1137-1147, Peking University, Beijing.
C.X. Lu, Synthesis of Polyesters Containing Nucleic Acid Base Derivatives as Pending Side Chains, Journal of Polymer Science: Part A: Polymer Chemistry, 1986, 24, 525-536, Peking University, Beijing.
Rulev A.Y. Russian Chemical Reviews, 2011, vol. 80, p. 197-218.
Atkins, et al., A Versatile Approach for the Syntheses of Poly(ester amide)s with pendant functional groups, Journal of Polymer Science Part A: Polymer Chemistry, vol. 47, No. 15, 3757-3772 (Aug. 2009).

* cited by examiner

MODIFICATION OF SEGMENTED POLYURETHANE PROPERTIES BY COPOLYMERIZING WITH PENDANT FUNCTIONALIZED DIOLS

CROSS-REFERENCE TO RELATED APPLICATION

This application is a continuation-in-part of U.S. patent application Ser. No. 16/297,933, filed on Mar. 11, 2019, which claims priority from U.S. provisional patent application Ser. No. 62/640,852 filed on Mar. 9, 2018, both of which are incorporated herein by reference.

STATEMENT REGARDING FEDERALLY SPONSORED RESEARCH OF DEVELOPMENT

This invention was made with government support under award number DMR-1352485 awarded by the National Science Foundation. The government has certain rights in the invention.

FIELD OF THE INVENTION

One or more embodiments of the invention provide modified segmented polyurethane polymers that include a plurality of pendant-functionalized amide units, and that are suitable for use in many types of medical devices and applications. Embodiments of the invention provide biocompatible, biodegradable polyurethane materials with controlled properties, such as thermal properties, mechanical properties, lubricity, antimicrobial properties, hydrophilicity, and anti-fouling properties.

BACKGROUND OF THE INVENTION

Segmented polyurethane elastomers, which are copolymers consisting of hard (glassy or semi crystalline) and soft (elastomeric) chain segments, have unique physical and mechanical properties and are known to be biocompatible and blood compatible, due to their hard-segment-soft-segment microphase structure, FIG. 1. For these reasons they are used for a number of biomedical applications.

High-purity medical segmented polyurethanes with a wide range of physical and chemical properties are used in various extracorporeal and implantable devices. The relatively poor molecular stability in the aggressive environment of the body tissues has been described. Susceptibility of polyurethanes to in vivo degradation can deliberately be exploited to design biodegradable polyurethane materials. Biodegradable polyurethanes can be synthesized by incorporating in the polymer chain labile moieties, susceptible to hydrolysis and/or to specific enzymes.

Depending on the mechanical properties, chemical composition and surface characteristics of biodegradable polyurethanes, they can potentially be used for cardiovascular implants, drug delivery devices, non-adhesive harriers in trauma surgery, bone graft substitutes, injectable augmentation materials, tissue-organ regeneration scaffolds (tissue engineering), or adhesives.

A common route for the synthesis of polyurethanes is described in Akindoyo, John O., Beg, M. D. H., Ghazali, Suriati, Islam, M. R., Jeyaratnam, Nitthiyah, and Yuvaraj, A. R., "Polyurethane Types, Synthesis and Applications—a Review," RSC Adv. 2016, 6, 114453-114482, which is hereby incorporated by reference. Schematically, the synthesis may be shown as follows:

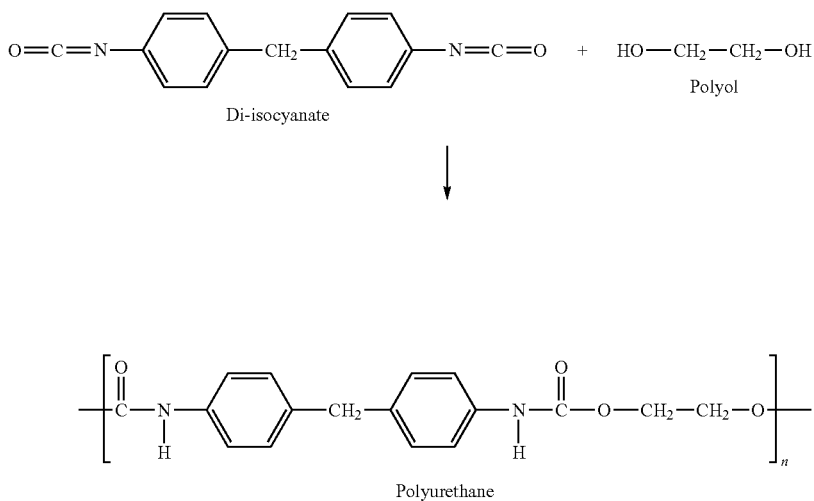

The type of monomers used in the syntheses of biodegradable polyurethanes will to a great extent be dependent on the intended application of the material. Various monomers have been incorporated into polyurethane polymers in order to provide beneficial properties, and these monomers are sometimes referred to as chain extenders. Some effects of various types and amounts of monomers on the mechanical and physical properties of polyurethane polymers are described in Kang, Jungmee, Erdodi, Gabor, and Kennedy, Joseph P., "Polyisobutylene-Based Polyurethanes with Unprecedented Properties and How They Came About," J. Poly. Science, Part A: Polymer Chemistry 2011, 49, 3891-3904, and U.S. Pat. No. 9,957,346, both of which are incorporated by reference herein. Biocompatible, biodegradable materials in the solid and/or liquid form based on the modification of segmented linear polyurethanes and/or segmented crosslinked polyurethanes are described in U.S. Pat. App. Pub. No. 2015/0231305 A1, which is incorporated by reference herein. Functionalized amide polymers having antimicrobial properties are described in U.S. Pat. App. Pub. No. 2017/0172147 A1, which is incorporated by reference herein.

Polyurethanes having a variety of properties, and the ability to further modify and even tailor the properties would be desirable. Currently, there is a lack of cost-effective methods for achieving this.

SUMMARY OF THE INVENTION

One or more embodiments of the present invention provide a functionalized polyurethane polymer, the polymer defined by the formula

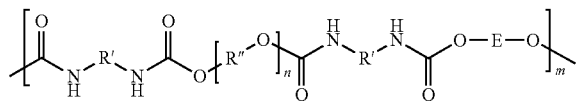

where each R' is independently derived from a diisocyanate, where each R" represents the soft segment of the polymer, where n is the number of repeat units within the soft segment of the polymer, where m is the number of repeating mer units in the polymer, where each E is a pendant-functionalized amide unit chain extender, wherein the nitrogen atom of the amide group is part of the polymer backbone, and wherein E may be represented by Formula 1A or 1B

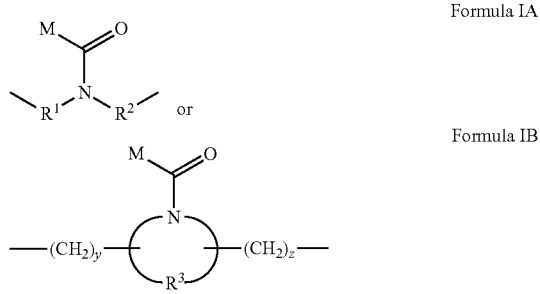

where $R^1$ and $R^2$ may be the same or different and are each hydrocarbon groups; $R^3$ is a heterocyclic group that includes the nitrogen atom as a hetero atom within the heterocyclic group; y and z may be the same or different and are from 0 to 4, and M is a pendant functional group.

One or more embodiments of the present invention further provide a cationic antimicrobial polyurethane polymer with anti-biofilm properties, the polymer defined by the formula

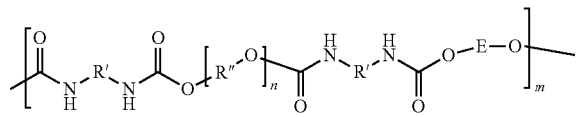

where each R' is independently derived from a diisocyanate, where each R" represents the soft segment of the polymer, where n is the number of repeat units within the soft segment of the polymer, where m is the number of repeating mer units in the polymer, where each E is a pendant-functionalized amide unit chain extender, wherein the nitrogen atom of the amide group is part of the polymer backbone, and wherein E may be represented by Formula 1A or 1B

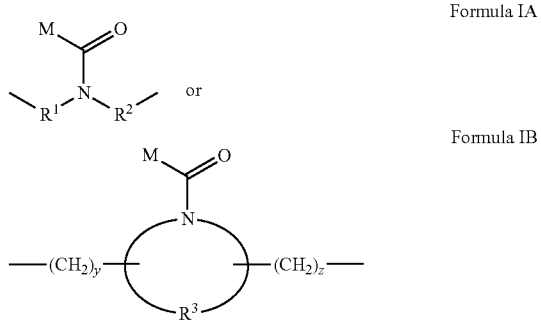

where $R^1$ and $R^2$ may be the same or different and are each hydrocarbon groups; $R^3$ is a heterocyclic group that includes the nitrogen atom as a hetero atom within the heterocyclic group; y and z may be the same or different and are from 0 to 4, and M is a cationic functional group.

One or more embodiments of the present invention further provide a method for preparing a segmented polyurethane polymer, the method comprising the steps of reacting a stoichiometric excess of a polyfunctional isocyanate with a polyol to yield a prepolymer; and reacting the prepolymer with a chain extender that is an N-substituted diol monomer having a pendant functional group that is attached through an amide bond.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF ILLUSTRATIVE EMBODIMENTS

Figure 1:
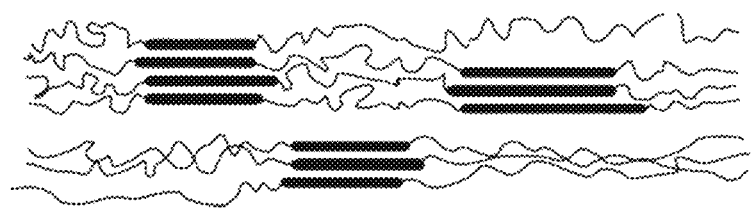
FIG. 1 is a schematic of a segmented polyurethane polymer system.

In the present invention, a segmented polyurethane polymer is provided that includes one or more units that comprise a pendant-functionalized amide chain extender. The pendant-functionalized amide unit is based upon the amide compounds described in U.S. Pat. No. 9,593,201, and Gokhale, Sachin, Xu, Ying, and Joy, Abraham. "A library of multifunctional polyesters with "peptide-like" pendant functional groups." Biomacromolecules, 2013, 14, 2489-2493, both of which are incorporated by reference herein. By reacting the pendant-functionalized diol monomer with a prepolymer containing terminal isocyanate groups to form a segmented polyurethane polymer, the properties of the segmented polyurethane polymer can be advantageously modified.

The segmented polyurethane polymers of the present invention are characterized in that each mer unit of the polymer includes one or more urethane linkages in the polymer chain:

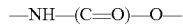

This type of linkage is sometimes referred to as a carbamate linkage. In one or more embodiments, the segmented polyurethane polymers of the present invention include at least two urethane linkages. The polymers also include at least one unit defined by the formula I

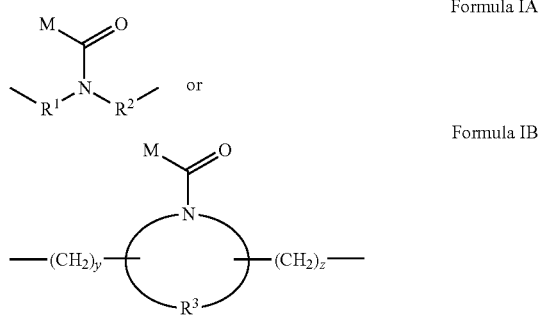

where $R^1$ and $R^2$ may be the same or different and are each hydrocarbon groups; $R^3$ is a heterocyclic group that includes the nitrogen atom as a hetero atom within the heterocyclic group; y and z may be the same or different and are from 0 to 4, and M is a pendant functional group.

M may be virtually any organic group. In one or more embodiments, M may be an organic pendant functional group. In one or more embodiments, M may be a cationic or anionic pendant functional group. In one or more embodiments, M may be an organic pendant functional group, but excluding fatty oils. In some embodiments, M is a group capable of reacting with other reagents to provide a desired functionality.

In one or more embodiments, M is selected from the group consisting of aliphatic and aromatic groups, aldehydes, amines, amino acids, azides, carboxylic acids, diols, furans, glucamine, halogens, hydroxyls, imaging labels, Jeffamine, ketones, maleimides, nitriles, polyalkylene oxides, polyalkylene glycols, peptides, propargyls, sugars, and thiols. In one or more embodiments, M is anionic or cationic, and may include one or more groups selected from carbonates, sulfates, phosphates, and ammonium.

In one or more embodiments, the segmented polyurethane polymer of the present invention includes a plurality of hard and soft segments. In one or more embodiments, each mer unit of the segmented polyurethane polymer includes hard and soft segments. The hard portion of the polymer generally derives from an isocyanate, and includes the urethane linkage. The hard segment also includes the pendant-functionalized amide chain extender. The soft segment is not particularly limited, so long as it provides flexibility or elasticity to the polymer.

In one or more embodiments, the segmented polyurethane polymer may be represented by the formula:

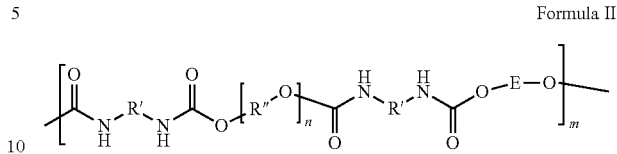

Formula II where each E is the pendant-functionalized amide unit chain extender, wherein the nitrogen atom of the amide group is part of the polymer backbone, and wherein E may be represented by Formula 1A or 1B, each R' is independently derived from a polyisocyanate, each R" represents the soft segment of the polymer, n is the number of repeat units within the soft segment of the polymer, and m is the number of repeating mer units in the polymer.

In one or more embodiments, each R' is independently selected from substituted or unsubstituted saturated aliphatic, saturated cycloaliphatic, and aromatic groups, with each group containing from 1 carbon atom, or the appropriate minimum number of carbon atoms to form the group, up to about 20 carbon atoms.

In one or more embodiments, R' is difunctional or trifunctional. In one or more embodiments, R' derives from an isocyanate selected from the group consisting of 1,6-hexamethylene diisocyanate, 1,4-diisocyanato butane, L-lysine diisocyanate, isophorone diisocyanate, 1,4-diisocyanato 2-methyl butane, 2,3-diisocyanato 2,3-dimethyl butane, 1,4-di(1propoxy-3-diisocyanate, 1,4-diisocyanato 2-butene, 1,10-diisocyanato decane, ethylene diisocyanate, 2,5 bis(2-isocyanato ethyl) furan, 1,6-diisocyanato 2,5-diethyl hexane, 1,6-diisocyanato 3-metoxy hexane, 1,5 diisocyanato pentane, 1,12-dodecamethylene diisocyanate, 2 methyl-2,4 diisocyanato pentane, 2,2 dimethyl-1,5 diisocyanato pentane, ethyl phosphonyl diisocyanate, 2,2,4-trimethyl-1,6-hexamethylene diisocyanate, 4,4'-diphenylmethane diisocyanate, 2,4'-diphenylmethane diisocyanate, 2,2'-diphenylmethane diisocyanate, 2,4-toluene diisocyanate, 2,4'-diphenylmethane diisocyanates, 4,4'-diphenylethane diisocyanato, 1,5-naphthylene diisocyanate, 5-isocyanato-1-(isocyanatomethyl)-1,3,3-trimethylcyclohexane (IPDI), toluene diisocyanate (TDI), 4,4'-Methylenebis(cyclohexyl isocyanate) (HMDI), and combinations thereof.

In Formula II above, R" represents the soft segment of the polymer. The soft segment of the polymer is not particularly limited. Nevertheless, essentially any component known and suitable for use as the soft, rubbery component of elastomers may be used, provided the component can be covalently bonded to the hard segments. Typically, such components are of higher molecular weight than those components found in the hard segment. For instance, the soft segment R" may derive from at least one moiety selected from the group consisting of polyols. Polyols include diols, as well and macrodiols. In one or more embodiments, R" may derive from two or more polyols.

Examples of polyols include polyether polyols, including polypropylene glycols, polyethylene glycols, and combinations and copolymers thereof, aliphatic polyester polyols, aromatic polyester polyols, polyether polyols based upon tetrahydrofuran, polycarbonate polyols, polycaprolactone polyols, acrylic polyols, polysulfide polyols, polybutadiene polyols, polysiloxane polyols, polyisobutylene polyols, and combinations and copolymers thereof.

In one or more embodiments, the molecular weight of the polyol is from about 100 to about 20,000 Da, in other embodiments, from about 400 to about 12,000 Da, in other embodiments, from about 600 to about 10,000 Da, in other embodiments, from about 1000 to about 8000 Da, in other embodiments, from about 1500 to about 7500 Da, and in other embodiments, from about 2000 to about 6000 Da.

The ratio of the hard to soft segments affects the properties of the polymer. In one or more embodiments, "n" in Formula I above is at least two, in other embodiments, at least three. In one or more embodiments, "n" is 100 or less, in other embodiments, 80 or less, in other embodiments, 50 or less. In one or more embodiments, "n" is from about 2 to about 100.

In one or more embodiments, the number average molecular weight of the polymer is from about 10 to about 300 kDa, in other embodiments, from about 12 to about 250, in other embodiments, from about 15 to about 150, in other embodiments, from about 20 to about 100 kDa. The molecular weight of the functionalized amide polymers of this invention may be determined through size exclusion chromatography. In one or more embodiments, the polymers may be characterized by a polydispersity of from about 1.1 to about 2.0.

In one or more embodiments, "m" in Formula I above is at least two, in other embodiments, at least three. In one or more embodiments, "n" is 100 or less, in other embodiments, 80 or less, in other embodiments, 50 or less. In one or more embodiments, "n" is from about 2 to about 100.

In one or more embodiments, the segmented polyurethane polymer may be a copolymer of two or more distinct mer units, each mer unit including a different pendant-functionalized amide unit chain extender. The mer units may be arranged in random or block configurations.

In one or more embodiments, the functionalized polyurethane polymer is defined by the formula

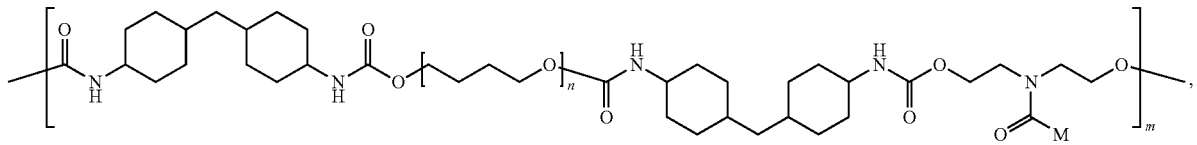

where n, m, and M are as defined above.

In one or more embodiments, M is a group represented by the formula

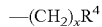

—(CH$_2$)$_x$R$^4$ where x is from 0 to 6, and where R$^4$ is a cationic group, an anionic group, or a hydroxyl group.

In one or more embodiments, the segmented polyurethane polymer is prepared in two steps. In the first step, a stoichiometric excess of a relatively small polyfunctional isocyanate (OCN—R'—NCO) is reacted with a polyol (HO—R"—OH) to yield a prepolymer, where R' and R" are as described above. The prepolymer may be thought of as a large diisocyanate, and may be represented by:

OCN—R'—NHCO—O—R"—O—CONH—R'—NCO.

In a second step, the prepolymer is chain extended by reacting the prepolymer with a chain extender that is an N-substituted diol monomer having a pendant functional group that is attached through an amide bond. In one or more embodiments, where the pendant-functionalized N-substituted diol monomer includes a protective group, the method may include a third step, where the protective group is removed to form the final polymer.

In one or more embodiments, the polyfunctional isocyanate is selected from diisocyanates, triisocyanates and polyisocyanates. The isocyanate may be used individually or as mixtures in various proportions. In one or more embodiments, the isocyanate is selected from the group consisting of 1,6-hexamethylene diisocyanate, 1,4-diisocyanato butane, L-lysine diisocyanate, isophorone diisocyanate, 1,4-diisocyanato 2-methyl butane, 2,3-diisocyanato 2,3-dimethyl butane, 1,4-di(1propoxy-3-diisocyanate, 1,4-diisocyanato 2-butene, 1,10-diisocyanato decane, ethylene diisocyanate, 2,5 bis(2-isocyanato ethyl) furan, 1,6-diisocyanato 2,5-diethyl hexane, 1,6-diisocyanato 3-metoxy hexane, 1,5 diisocyanato pentane, 1,12-dodecamethylene diisocyanate, 2 methyl-2,4 diisocyanato pentane, 2,2 dimethyl-1,5 diisocyanato pentane, ethyl phosphonyl diisocyanate, 2,2,4-trimethyl-1,6-hexamethylene diisocyanate, 4,4'-diphenylmethane diisocyanate, 2,4'-diphenylmethane diisocyanate, 2,2'-diphenylmethane diisocyanate, 2,4-toluene diisocyanate, 2,4'-diphenylmethane diisocyanates, 4,4'-diphenylethane diisocyanato, 1,5-naphthylene diisocyanate, 5-isocyanato-1-(isocyanatomethyl)-1,3,3-trimethylcyclohexane (IPDI), toluene diisocyanate (TDI), 4,4'-Methylenebis(cyclohexyl isocyanate) (HMDI), and combinations thereof.

In one or more embodiments, the polyol is as described hereinabove for R". In one or more embodiments, the polyol is selected from the group consisting of polyether polyols, including polypropylene, polyethylene, and combinations and copolymers thereof, aliphatic polyester polyols, aromatic polyester polyols, polyether polyols based upon tetrahydrofuran, polycarbonate polyols, polycaprolactone polyols, acrylic polyols, polysulfide polyols, polybutadiene polyols, polysiloxane polyols, polyisobutylene polyols, and combinations and copolymers thereof. In one or more embodiments, the polyol is selected from polyesters, polyethers, mixtures thereof, and copolymers of esters with ethers. In one or more embodiments, the polyol is selected from biocompatible polyols.

Examples of polyols include 1,4-butanediol, diethylene diol, 1,5-hexanediol 1,3-propanediol, neopentyl diol, trimethylene diol, and pentaerythritol. Further examples include polycarbonate diols, polyisobutylene diols, poly(ε-caprolactone) diols, poly(ethylene oxide) diols, poly(ethylene oxide-propylene oxide-ethylene oxide) diols, polyols based on β-propiolactone, δ-valerolactone and γ-butyrolactone, isosorbide, aminosaccharides, and polyols from vegetable oils such as stearic, oleic, linoleic and linolenic. Combinations of the aforesaid examples may also be employed.

In one or more embodiments, the molecular weight of the polyol is from about 100 to about 20,000 Da, in other embodiments, from about 400 to about 12,000 Da, in other embodiments, from about 600 to about 10,000 Da, in other embodiments, from about 1000 to about 8000 Da, in other embodiments, from about 1500 to about 7500 Da, and in other embodiments, from about 2000 to about 6000 Da.

In one or more embodiments, the chain extender is an N-substituted diol monomer having a pendant functional group that is attached through an amide bond. In one or more embodiments, the N-substituted diol monomer having a pendant functional group is defined by formulas (III) and (IV):

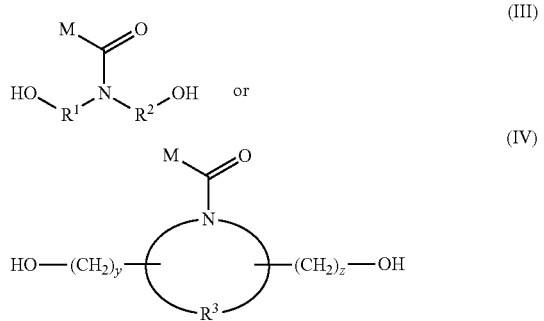

where $R^1$ and $R^2$ may be the same or different and are each hydrocarbon groups; $R^3$ is a heterocyclic group that includes the nitrogen atom as a hetero atom within the heterocyclic group, and y and z may be the same or different and are from 0 to 4, and M is a pendant functional group as described above. It will be appreciated that the formulas (III) and (IV) can be conceptualized as being related, in that the $R^1$ and $R^2$ of formula (III) join to create a heterocyclic group represented by $R^3$, the heterocyclic group including the nitrogen atom as a hetero atom within the heterocyclic group.

In one or more embodiments, $R^1$ and $R^2$ are hydrocarbon chains of length from 1 to 10 carbon atoms (C1 to C10). In one or more embodiments, $R^1$ and $R^2$ are hydrocarbon chains from 1 to 6 carbon atoms (C1 to C6). In one or more embodiments, $R^1$ and $R^2$ are hydrocarbon chains from 1 to 3 carbons atoms (C1 to C3).

In one or more embodiments, $R^3$ is an organic group that forms a heterocycle with the nitrogen atom. In one or more embodiments, the organic group of $R^3$ may include oxygen as a heteroatom. In one or more embodiments, the organic group of $R^3$ is a hydrocarbon group. In one or more embodiments, $R^3$ is a hydrocarbon chain from 2 to 5 carbon atoms. In one or more embodiments, $R^3$ is a hydrocarbon chain from 4 to 5 carbon atoms. In one or more embodiments, $R^3$ is a hydrocarbon chain of about 4 carbon atoms.

As described above, M may be virtually any organic group. In one or more embodiments, M may be an organic pendant functional group. In one or more embodiments, M may be a cationic or anionic pendant functional group. In one or more embodiments, M may be an organic pendant functional group, but excluding fatty oils. In some embodiments, M is a group capable of reacting with other reagents to provide a desired functionality in a post-polymerization functionalization step that will be described herein. In other embodiments, M includes a protecting group that protects the M group from reacting with other reagents during monomer creation or polymer creation or both or during post functionalization steps, particularly with multifunctional polymers as described herein.

In one or more embodiments, M may be a group selected from aliphatic and aromatic groups, aldehydes, amines, amino acides, azides, carboxylic acids, diols, furans, glucamine, halogens, hydroxyls, imaging labels, Jeffamine, ketones, maleimides, nitriles, polyalkylene oxides, polyalkylene glycols, peptides, propargyls, sugars, and thiols.

In one or more embodiments, M may be a group represented by the formula

—$(CH_2)_xR^4$ where x is from 0 to 6, and where $R^4$ is a cationic group, an anionic group, or a hydroxyl group. In one or more embodiments, $R^4$ includes one or more groups selected from carbonates ($CO_2^-$), phosphates ($PO_4^{2-}$), sulfates ($SO_4^{2-}$), ammonium ($NH_3^+$), hydroxyl (OH), and combinations thereof.

Representative examples of organic pendant functional groups include but are not limited to:

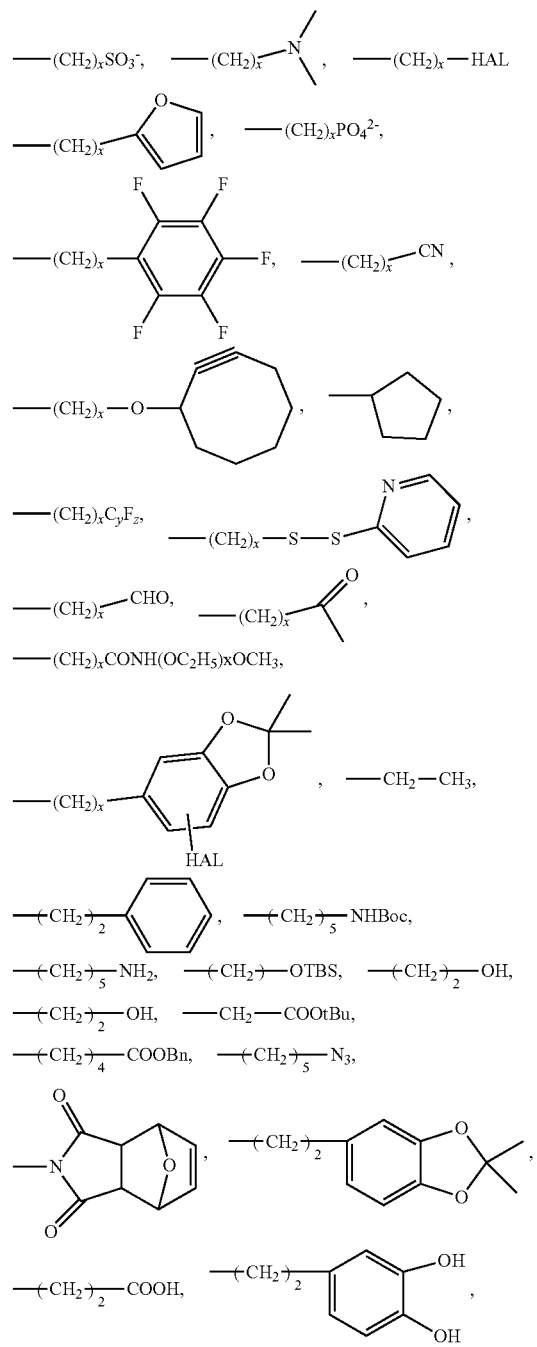

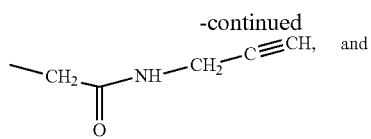

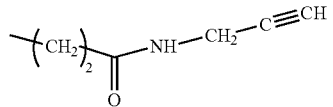

wherein x is from 0 to 6, and HAL denotes a halogen. It is specifically noted that, though specific numbers are provided for repeating units of —$CH_2$— in some of the above structures, the present invention can be practiced with x repeating units of those structures. Herein, it will be understood that Boc stands for tert-butyloxycarbonyl, TBS stands for ditertbutyl dimethylsilyl, tBu stands for t-Butyl, Bn stands for benzyl.

In one or more embodiments, M may be selected to be a group that is capable of reacting with other reagents to provide a desired functionality in a post-polymerization functionalization step.

Representative examples of groups suitable for post polymerization functionalization include groups with azide, carboxylic acid, hydroxyl, amine, nitrile, furan, aldehyde/ketone, maleimide, propargyl, or halogen functionality. Particular non-limiting examples include:

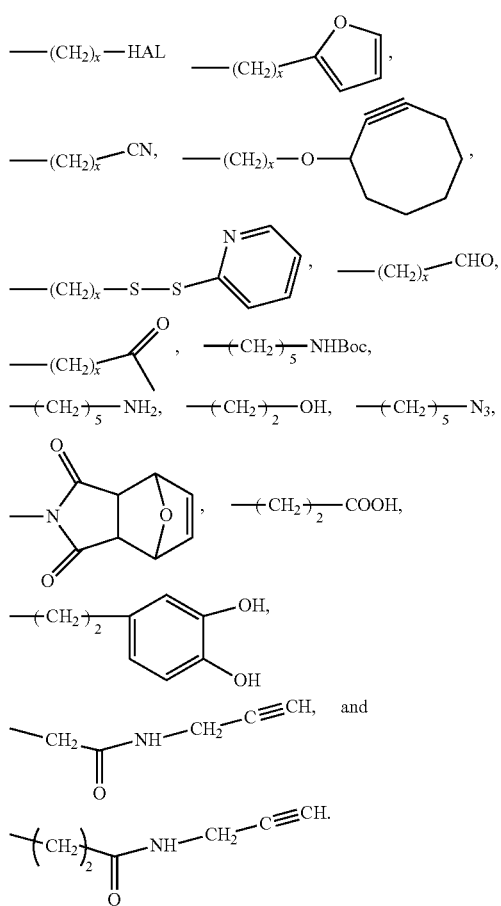

Representative examples of protected groups include M groups protected with tert-butyloxycarbonyl, pyridyl disulfide, t-Butyl, benzyl, ketal, and ditertbutyl dimethylsilyl. Non-limiting examples include:

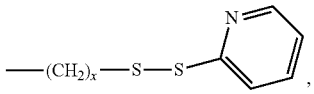

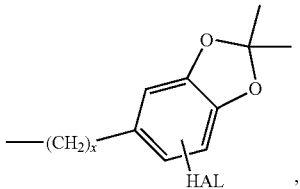

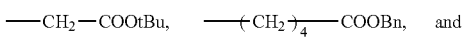

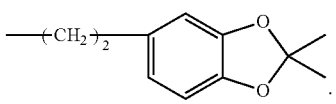

In one or more embodiments, M may be an amino acid side chain. An amino acid side chain is a group that includes a terminal functional group of an amino acid. In one or more embodiments, the terminal functional group of the amino acid is attached to a carbon chain or connecting group. In some embodiments, the carbon chain is a different length than the chain of the corresponding amino acid. Representative examples of residues of an amino acid side chain include, but are not limited to:

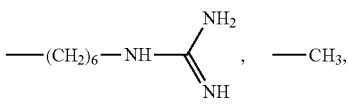

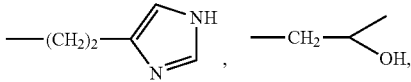

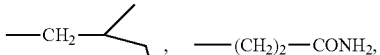

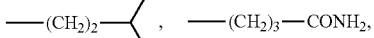

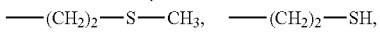

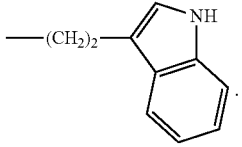

The nitrogen atom of the chain extender is part of the polymer backbone, such that the polyurethane polymers herein can be generally conceptualized by the structure below:

where ⁓⁓⁓⁓⁓ generally represents the polyurethane polymer backbone and M is as described herein.

The pendant functional groups of the chain extender may be advantageously selected to modulate the physical, chemical and biological properties of the polymers. In one or more embodiments, the polyurethane polymers of the present invention may be further modified by reaction of the pendant functional group, such as conjugation of dyes, drugs, peptides, zwitterionic compounds such as quaternary ammonium compounds and phosphorylcholine, or other functional components. In one or more embodiments, a fluorescent dye such as FITC may be reacted with M to provide or modify fluorescent properties.

In one or more embodiments, the pendant functional groups may be used to alter the solubility of polymer.

In the example section herein specific data is given regarding the effect of pendant groups on water contact angles and Tg.

Depending on the chemical composition, elastic properties, hydrophilicity, degradation rates and porosity, the polyurethanes of the invention can be used as adhesion barriers, scaffolds for the repair and regeneration of various tissues, solid tissue defect fillers and liquid injectable materials which solidify after injection. In one or more embodiments, the polymers of the present invention are useful in many applications, such as drug delivery, scaffolds, biosensors and diagnostics, medical implants, antimicrobial membranes, skin tissue repair, or vascular grafts.

In order to demonstrate the practice of the present invention, the following examples have been prepared and tested. The examples should not, however, be viewed as limiting the scope of the invention. The claims will serve to define the invention.

EXAMPLES

Figure 2:
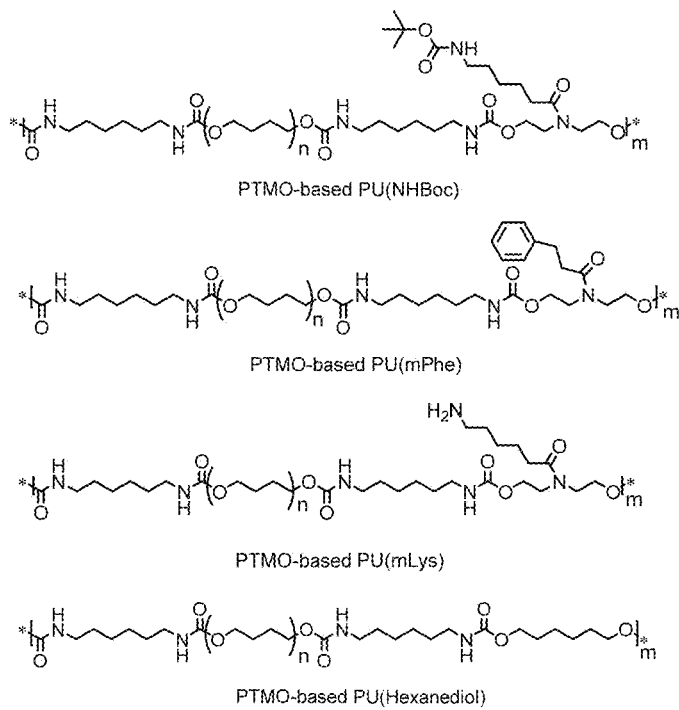
FIG. 2 is a graphical summary of poly(tetramethylene oxide) (PTMO) based polyurethanes with various pendant-functionalized amide units and their contact angles.
Figure 2:
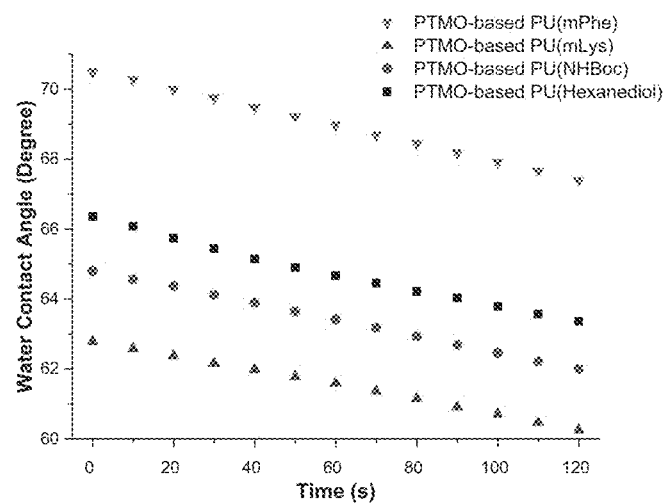

Poly(tetramethylene oxide) (PTMO) based polyurethanes were synthesized using various diols containing an N-functionalized amide group. It was found that the identity of the pendant group influenced physical properties such as hydrophilicity, as indicated by the water contract angle. (FIG. 2). Generally, to synthesize these polyurethanes, a prepolymer was first synthesized by reacting poly(tetramethylene oxide) (PTMO) diol with hexamethylene diisocyanate catalyzed by dibutyltin dilaurate (DBTDL) at 50° C. for 4 hours. The resulting prepolymer was polymerized with a diol containing an N-functionalized amide group in the presence of DBTDL at room temperature for 24 hours to give a polyurethane polymer that includes a pendant-functionalized amide chain extender.

These pendant-functionalized chain extenders can also be incorporated into the composition of commercial polyurethanes, including, but not limited to, Tecoflex®, Pellethane®, and BioSpan®, to provide various properties. For example, a pendant-functionalized amide unit was incorporated into the composition of Tecoflex® (Scheme 1) to provide antimicrobial properties.

Scheme 1

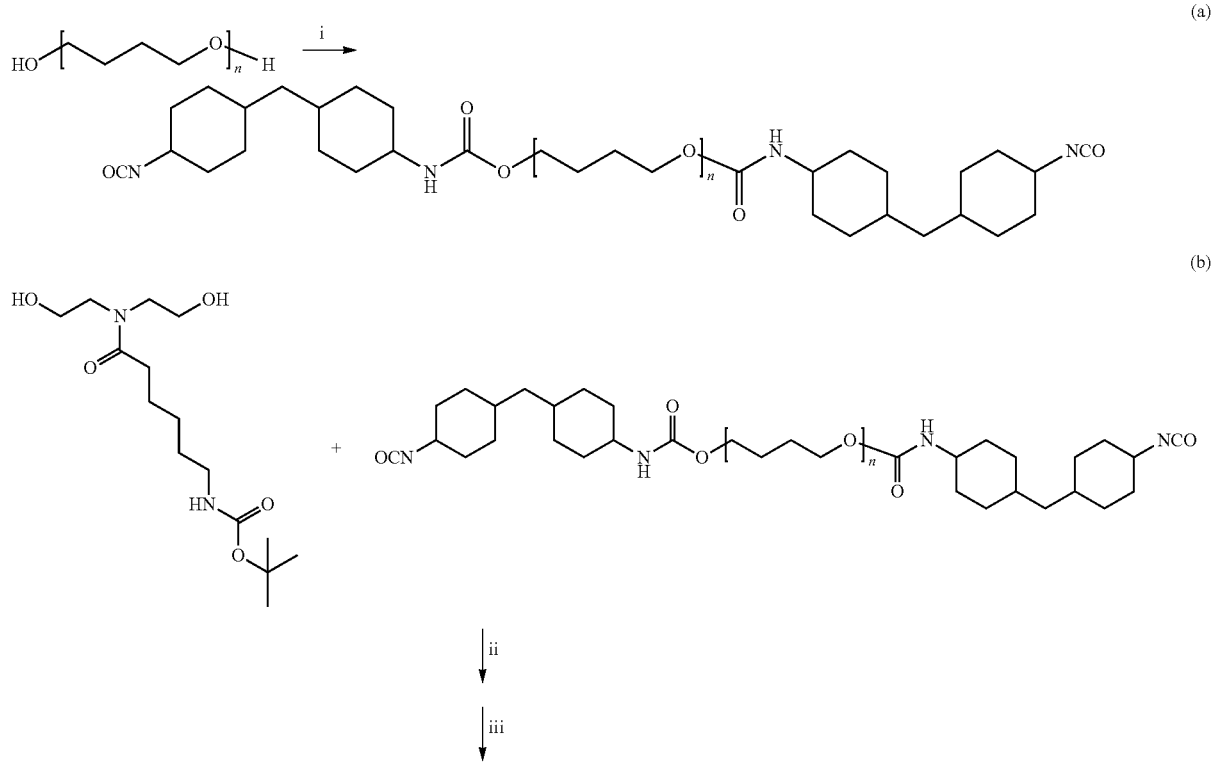

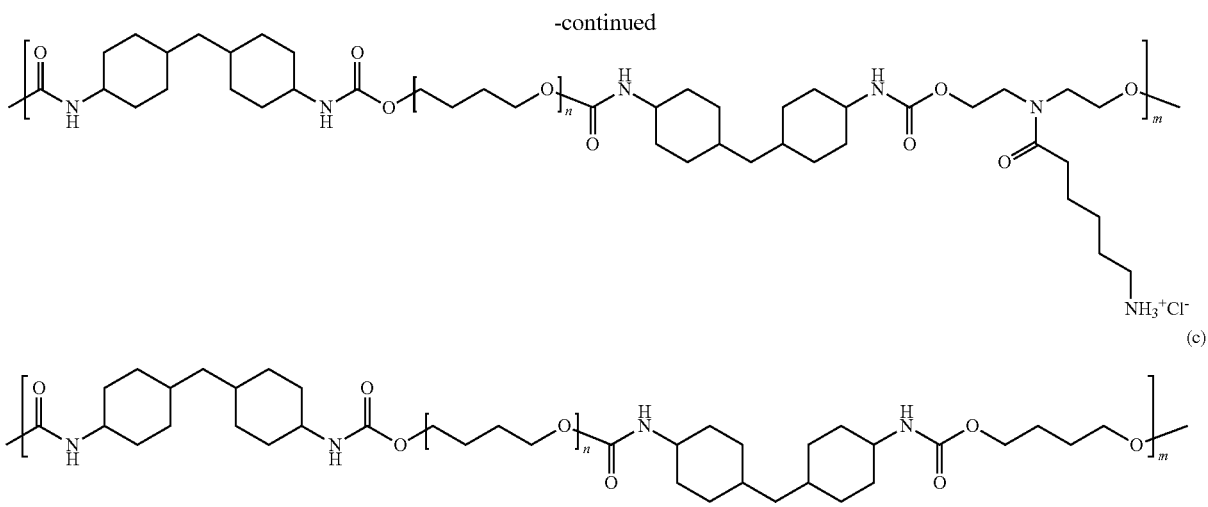

(c)

The amine functionalized polyurethane was synthesized via a three-step reaction (Scheme 1). Shown in Scheme 1 is the synthetic route for the preparation of (a) prepolymer and (b) amine functionalized polyurethane Tecoflex-$NH_3$+. Tecoflex® is shown in (c), and was synthesized by polymerizing the prepolymer with 1,4-butanediol. Reagents and conditions: (i) 4,4'-methylenebis(cyclohexyl isocyanate), $CH_2Cl_2$, DBTDL, 50° C., 4 hours; (ii) $CH_2Cl_2$, DBTDL, room temperature, 24 hours; (iii) 4 N HCl in 1,4-dioxane, $CH_2Cl_2$, 45 min. More specifically, first, a prepolymer was made by reacting 4,4'-methylenebis(cyclohexyl isocyanate) (HMDI) with poly(tetramethylene oxide) (PTMO) in the presence of di-butyltin dilaurate (DBTDL) at 50° C. for 4 hours. The resulting prepolymer was then copolymerized with the diol containing an N-functionalized amide group, catalyzed by DBTDL at room temperature for 24 hours. The resulting polymer was deprotected with 4 N HCl in 1,4-dioxane/$CH_2Cl_2$ to give the final product.

Similarly, the non-functionalized Tecoflex® was synthesized by copolymerizing the prepolymer with 1,4-butanediol under the same conditions. The chemical structure of the polymers was confirmed by IR and $^1$H NMR spectroscopy. As determined by DMF GPC, the molecular weights of Tecoflex® and Tecoflex-$NH_3$+ were 41.5 and 30.7 kDa, respectively. The Tecoflex-$NH_3$+ surface exhibited lower contact angle (80°) compared to the non-functionalized Tecoflex® surface (92°), which can be attributed to the presence of cationic groups on the surface. As shown by the DSC data, both Tecoflex® and Tecoflex-$NH_3$+ showed similar glass transition temperatures (Tg) (~−75° C.). Tecoflex® exhibited a melting peak (Tm) at 17° C., while Tecoflex-$NH_3$+ was amorphous due to the incorporated pendant functional groups. Since the Tm of Tecoflex® is lower than room temperature, the effect of the different crystallization behavior on the performance of the two polymers is likely to be minimal because both polymers were amorphous under the test condition (37° C.). To further confirm this, we performed 1H solid-state magic-angle spinning (MAS) NMR spectroscopy at 298 K to evaluate the crystallinity of the two polymers. Typically, crystalline polymers will show broad peaks while amorphous polymers will show narrow peaks, reflecting the mobility of amorphous chains. $^1$H MAS NMR spectra for both samples showed only narrow peaks, demonstrating the amorphous nature of both samples at the test conditions.

Figure 3:
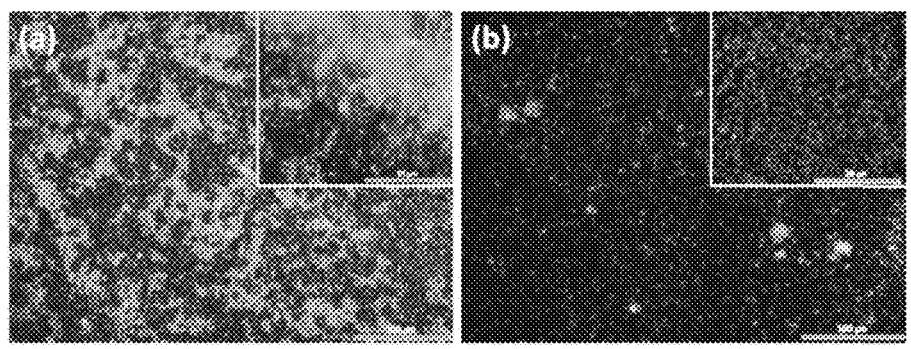
FIG. 3 is a micrograph showing live/dead staining of *E. coli* on Tecoflex® (a) and Tecoflex-NH3+ (b) after 24 hours incubation.
Figure 4:
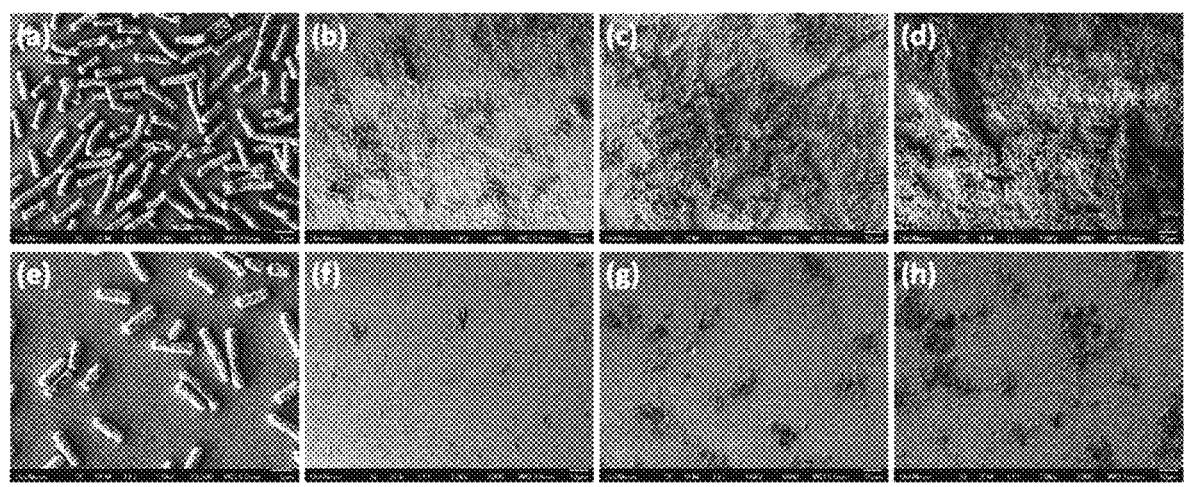
FIG. 4 is scanning electron microscope (SEM) images of Tecoflex® coating after incubation with *E. coli* suspension for 1 day (a, b), 3 days (c), and 5 days (d); SEM images of Tecoflex-NH3 coating after incubation with *E. coli* suspension for 1 day (e, f), 3 days (g), and 5 days (h). The scale bars in a, e are 1 micrometers (μm), and the scale bars in b, c, d, f, g, h are 10 μm.

As shown by the live-dead staining in FIG. 3, these cationic polyurethanes showed good antimicrobial properties. Catheter-associated urinary tract infections are frequently caused by fecal *E. coli*, as further discussed and described in Peng, Chao, Vishwakarma, Apoorva, Li, Zhuoran, Miyoshi, Toshikazu, Barton, Hazel A., and Joy, Abraham, "Modification of a Conventional Polyurethane Composition Provides Significant Anti-biofilm Activity Against *Escherichia coli*", Polym. Chem., 2018, 9, 3195-3198, which is incorporated by reference herein. The ability of polyurethane coatings to prevent *E. coli* biofilm formation was tested as follows. The biofilm forming *E. coli* strain 25 922, was used to evaluate biofilm formation. To determine the effect of the polyurethane coatings on *E. coli* colonization, polymer coated cover-slips were incubated with an *E. coli* suspension in M9 minimal medium at 37° C. for 24 hours. After 1 day, bacterial colonization and viability were determined by live-dead staining using fluorescence microscopy, in which live bacteria fluoresce green and dead bacteria fluoresce red. As shown in FIG. 3(a), a large area of viable biofilm was seen on the Tecoflex® surface, as shown by the green fluorescence. In contrast to the non-functionalized surface, there were significantly fewer bacterial colonies on the functionalized surface (Tecoflex-NH+), and most of the attached bacteria were dead, as evidenced by red fluorescence in FIG. 3(b). The SEM images in FIG. 4 show significant decrease in bacteria colonization on the cationic amine polyurethanes.

Figure 5:
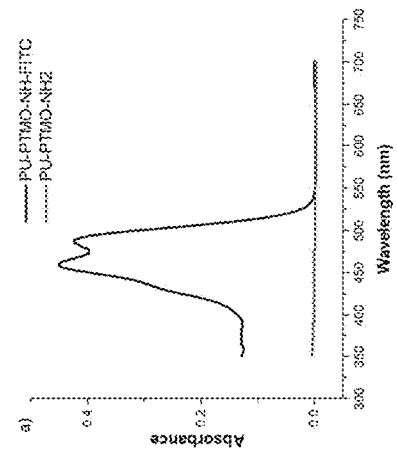
FIG. 5 is a schematic of the post-polymerization functionalization of pendant-functionalized polyurethane with the fluorophore FITC.
Figure 5:
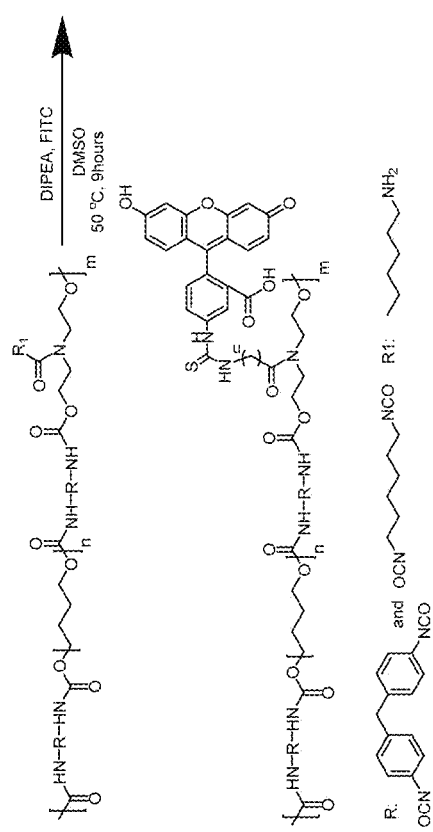

To illustrate that the polyurethane polymers containing the pendant-functionalized amide group can be further functionalized, the following experiment was undertaken. Fluorescein isothiocyanate (FITC) was attached to the amine functionalized polyurethane polymer described above, according to the scheme shown in FIG. 5. UV absorbance of the FITC functionalized polyurethane was measured, as shown in FIG. 5.

As shown above, a cationic antimicrobial polyurethane was designed and developed by incorporating an amine functionalized N-substituted diol to obtain a compositional variant of the commercial polyurethane Tecoflex®. The peptidomimetic cationic functionalities were incorporated into a polyurethane polymer through copolymerization with the N-substituted diol monomer having a pendant functional group that is attached through an amide bond. This novel cationic polyurethane, Tecoflex-$NH_3$+, exhibited a contactkilling mechanism and showed excellent anti-biofilm properties against *E. coli* even after 5 days. In addition, this cationic polyurethane has good selectivity against *E. coli* over mammalian cells, as depicted by very low hemolytic activity and cytotoxicity.

In one or more embodiments, the N-substituted diol monomer having a pendant functional group that is attached through an amide bond is useful in other step-growth polymer platforms, wherein the monomer is copolymerized with other monomers and polymer, and its incorporation into the copolymer confers antimicrobial properties to the copolymer. Small structural changes in the polymer compositions used for catheter fabrication, such as shown herein, can provide significant antibacterial properties.

Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. A functionalized polyurethane polymer defined by the formula

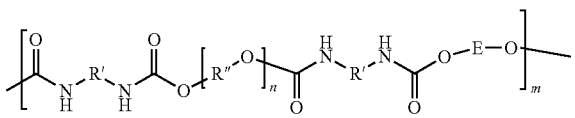

where each R' is independently derived from a diisocyanate containing R', where each R" represents a soft segment of the polymer and is independently derived from a polyol containing R", where n is the number of repeat units within the soft segment of the polymer, where m is the number of repeating mer units in the polymer, where each E is a pendant-functionalized amide unit chain extender derived from an N-substituted diol monomer containing E, wherein the nitrogen atom of the amide group is part of the polymer backbone, and wherein E is represented by Formula 1A or 1B

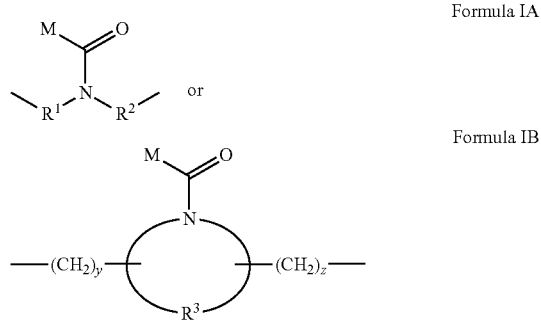

where $R^1$ and $R^2$ may be the same or different and are each hydrocarbon groups; $R^3$ is a heterocyclic group that includes the nitrogen atom as a hetero atom within the heterocyclic group; y and z may be the same or different and are from 0 to 4, and M is a pendant functional group represented by the formula —$(CH_2)_x R^4$ where x is from 0 to 6, and where $R^4$ is a cationic group, an anionic group, or a hydroxyl group.

2. The functionalized polyurethane polymer of claim 1, where the polymer has a number molecular weight of at least 10 kDa.

3. The functionalized polyurethane polymer of claim 1, where each R' is independently selected from the group consisting of substituted or unsubstituted saturated aliphatic groups, saturated cycloaliphatic groups, and aromatic groups, with each group independently containing from 1 carbon atom, or the appropriate number of carbon atoms to form the group, up to about 20 carbon atoms.

4. The functionalized polyurethane polymer of claim 1, where each R' is independently derived from a diisocyanate selected from the group consisting of 1,6-hexamethylene diisocyanate, 1,4-diisocyanato butane, L-lysine diisocyanate, isophorone diisocyanate, 1,4-diisooyanato 2-methyl butane, 2,3-diisocyanato 2,3-dimethyl butane, 1,4-di (1propoxy-3-diisocyanate, 1,4-diisocyanato 2-butene, 1,10-diisocyanato decane, ethylene diisocyanate, 2,5 bis(2-isocyanato ethyl) furan, 1,6-diisocyanato 2,5-diethyl hexane, 1,6-diisocyanato 3-methoxy hexane, 1,5 diisocyanato pentane, 1,12-dodecamethylene diisocyanate, 2 methyl-2,4 diisocyanato pentane, 2,2 dimethyl-1,5 diisocyanato pentane, ethyl phosphonyl diisocyanate, 2,2,4-trimethyl-1,6-hexamethylene diisocyanate, 4,4'-diphenylmethane diisocyanate, 2,4'-diphenylmethane diisocyanate, 2,2'-diphenylmethane diisocyanate, 2,4-toluene diisocyanate, 2,4'-diphenylmethane diisocyanates, 4,4'-diphenylethane diisocyanato, 1,5-naphthylene diisocyanate, 5-isocyanato-1-(isoeyanatomethyl)-1,3,3-trimethylcyclohexane (IPDI), toluene diisocyanate (TDI), and 4,4'-Methylenebis(cyclohexyl isocyanate) (HMDI).

5. The functionalized polyurethane polymer of claim 1, where each R" is independently derived from a polyol selected from the group consisting of 1,4-butanediol, diethylene diol 1,5-hexanediol, 1,3-propanediol, neopentyl diol, trimethylene diol, pentaerythritol polyether polyols, aliphatic polyester polyols, aromatic polyester polyols, polyether polyols based upon tetrahydrofuran, polycarbonate polyols, polycaprolactone polyols, acrylic polyols, polysulfide polyols, polybutadiene polyols, polysiloxane polyols, poly isobutylene polyols, and copolymers thereof.

6. The functionalized polyurethane polymer of claim 1, where each R" independently contains from 1 to about 20 carbon atoms.

7. The functionalized polyurethane polymer of claim 1, where n is from about 2 to about 100.

8. The functionalized polyurethane polymer of claim 1, where m is from about 2 to about 100.

9. The functionalized polyurethane polymer of claim 1, where the polymer is defined by the formula

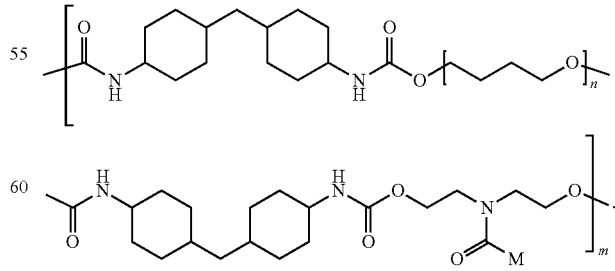

10. A method for preparing the functionalized polyurethane polymer of claim 1, the method comprising the steps of:

reacting a stoichiometric excess of at least one diisocyanate containing R' with at least one polyol containing R" to yield a prepolymer; and reacting the prepolymer with a chain extender that is an N-substituted diol monomer containing E.

11. The method of claim 10, where each of the at least one diisocyanate containing R' is defined by the formula OCN—R'—NCO, where each R' is independently selected from the group consisting of substituted or unsubstituted saturated aliphatic groups, saturated cycloaliphatic groups, and aromatic groups, with each group independently containing from 1 to about 20 carbon atoms.

12. The method of claim 10, where each of the at least one diisocyanate containing R' is independently selected from the group consisting of 1,6-hexamethylene diisocyanate, 1,4-diisocyanato butane, L-lysine diisocyanate, isophorone diisocyanate, 1,4-diisooyanato 2-methyl butane, 2,3-diisocyanato 2,3-dimethyl butane, 1,4-di(1propoxy-3-diisocyanate, 1,4-diisocyanato 2-butene, 1,10-diisocyanato decane, ethylene diisocyanate, 2,5 bis(2-isocyanato ethyl) furan, 1,6-diisocyanato 2,5-diethyl hexane, 1,6-diisocyanato 3-methoxy hexane, 1,5 diisocyanato pentane, 1,12-dodecamethylene diisocyanate, 2 methyl-2,4 diisocyanato pentane, 2,2 dimethyl-1,5 diisocyanato pentane, ethyl phosphonyl diisocyanate, 2,2,4-trimethyl-1,6-hexamethylene diisocyanate, 4,4'-diphenylmethane diisocyanate, 2,4'-diphenylmethane diisocyanate, 2,2'-diphenylmethane diisocyanate, 2,4-toluene diisocyanate, 2,4'-diphenylmethane diisocyanates, 4,4'-diphenylethane diisocyanato, 1,5-naphthylene diisocyanate, 5-isocyanato-1-(isoeyanatomethyl)-1,3,3-trimethylcyclohexane (IPDI), toluene diisocyanate (TDI), and 4,4'-Methylenebis(cyclohexyl isocyanate) (HMDI).

13. The method of claim 10, where each of the at least one polyol containing R" is defined by the formula HO—R"—OH, where each R" independently contains from 1 to about 20 carbon atoms.

14. The method of claim 10, where each of the at least one polyol containing R" is independently selected from the group consisting of 1,4-butanediol, diethylene diol 1,5-hexanediol, 1,3-propanediol, neopentyl diol, trimethylene diol, pentaerythritol polyether polyols, aliphatic polyester polyols, aromatic polyester polyols, polyether polyols based upon tetrahydrofuran, polycarbonate polyols, polycaprolactone polyols, acrylic polyols, polysulfide polyols, polybutadiene polyols, polysiloxane polyols, poly isobutylene polyols, and copolymers thereof.

15. The method of claim 10, where the prepolymer is defined by:

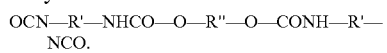
OCN—R'—NHCO—O—R"—O—CONH—R'—NCO.

16. A functionalized polyurethane polymer defined by the formula

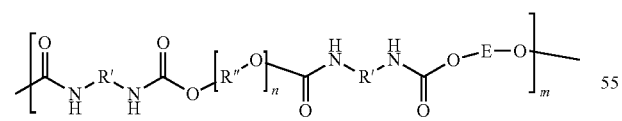

where each R' is independently derived from a diisocyanate containing R', where each R" represents a soft segment of the polymer and is independently derived from a polyol containing R", where n is the number of repeat units within the soft segment of the polymer, where m is the number of repeating mer units in the polymer, where each E is a pendant-functionalized amide unit chain extender derived from an N-substituted diol monomer containing E, wherein the nitrogen atom of the amide group is part of the polymer backbone, and wherein E is represented by Formula 1A or 1B

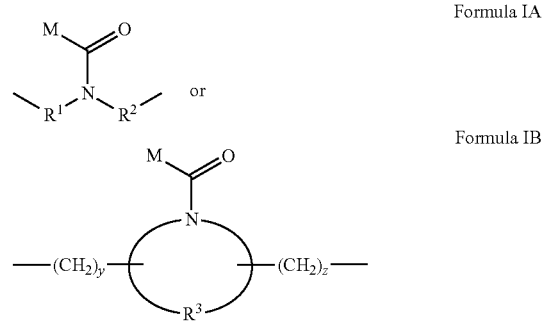

Formula IA

Formula IB where $R^1$ and $R^2$ may be the same or different and are each hydrocarbon groups; $R^3$ is a heterocyclic group that includes the nitrogen atom as a hetero atom within the heterocyclic group; y and z may be the same or different and are from 0 to 4, and M is a pendant functional group that includes one or more groups selected from carbonates ($CO_2^-$), phosphates ($PO_4^{2-}$), sulfates ($SO_4^{2-}$), ammonium ($NH_3^+$), and hydroxyl (OH).

17. A cationic antimicrobial polyurethane polymer with anti-biofilm properties, the polymer defined by the formula

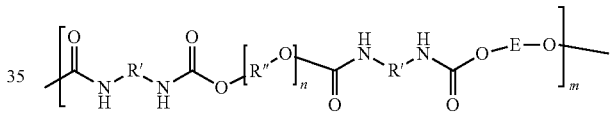

where each R' is independently derived from a diisocyanate containing R', where each R" represents a soft segment of the polymer and is independently derived from a polyol containing R", where n is the number of repeat units within the soft segment of the polymer, where m is the number of repeating mer units in the polymer, where each E is a pendant-functionalized amide unit chain extender derived from an N-substituted diol monomer containing E, wherein the nitrogen atom of the amide group is part of the polymer backbone, and wherein E is represented by Formula 1A or 1B

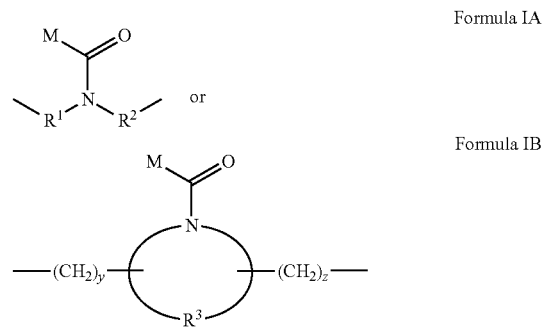

Formula IA

Formula IB where $R^1$ and $R^2$ may be the same or different and are each hydrocarbon groups; $R^3$ is a heterocyclic group that includes the nitrogen atom as a hetero atom within the heterocyclic group; y and z may be the same or different and are from 0 to 4, and M is a cationic functional group.
18. The polymer of claim 17, where the polymer is defined by the formula
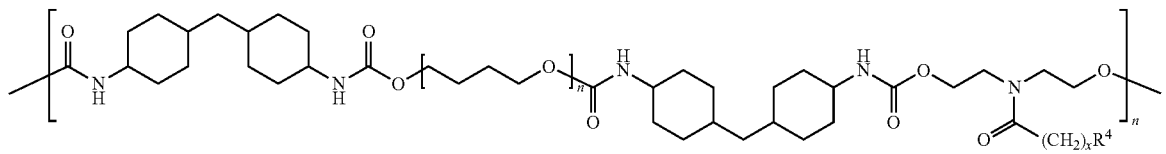
where x is from 0 to 6, and where $R^4$ is a cationic group.
19. The polymer of claim 17, where the polymer is defined by the formula
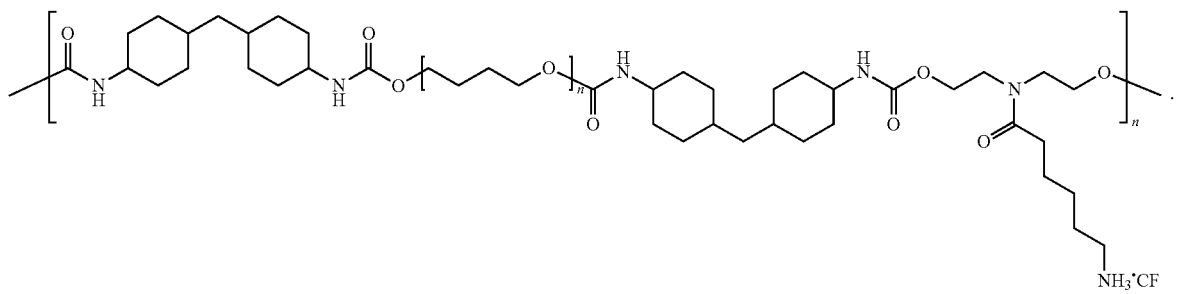
* * * * *